US00PP29683P3

(12) United States Plant Patent
Woods

(10) Patent No.: US PP29,683 P3
(45) Date of Patent: Sep. 18, 2018

(54) ***HIBISCUS* PLANT NAMED 'RWOODS5'**

(50) Latin Name: *Hibiscus syriacus*
Varietal Denomination: RWOODS5

(71) Applicant: Roderick Ian Woods, King's Lynn (GB)

(72) Inventor: Roderick Ian Woods, King's Lynn (GB)

(73) Assignee: Spring Meadows Nursery, Inc., Grand Haven, MI (US)

( * ) Notice: Subject to any disclaimer, the term of this patent is extended or adjusted under 35 U.S.C. 154(b) by 28 days.

(21) Appl. No.: 15/330,684

(22) Filed: Oct. 25, 2016

(65) Prior Publication Data

US 2018/0116085 P1 Apr. 26, 2018

(51) Int. Cl.
*A01H 5/02* (2018.01)

(52) U.S. Cl.
USPC ..... Plt./257

(58) Field of Classification Search
USPC ..... Plt./257
See application file for complete search history.

*Primary Examiner* — Keith O Neal Robinson
(74) *Attorney, Agent, or Firm* — Cassandra Bright

(57) ABSTRACT

A new and distinct *Hibiscus* cultivar named 'RWOODS5' is disclosed, characterized by large, fully double magenta flowers up to 10 cm in diameter. Plants are floriferous and tolerate wet conditions well. The new variety is a *Hibiscus*, normally produced as an outdoor garden or container plant.

2 Drawing Sheets

Figure 1:
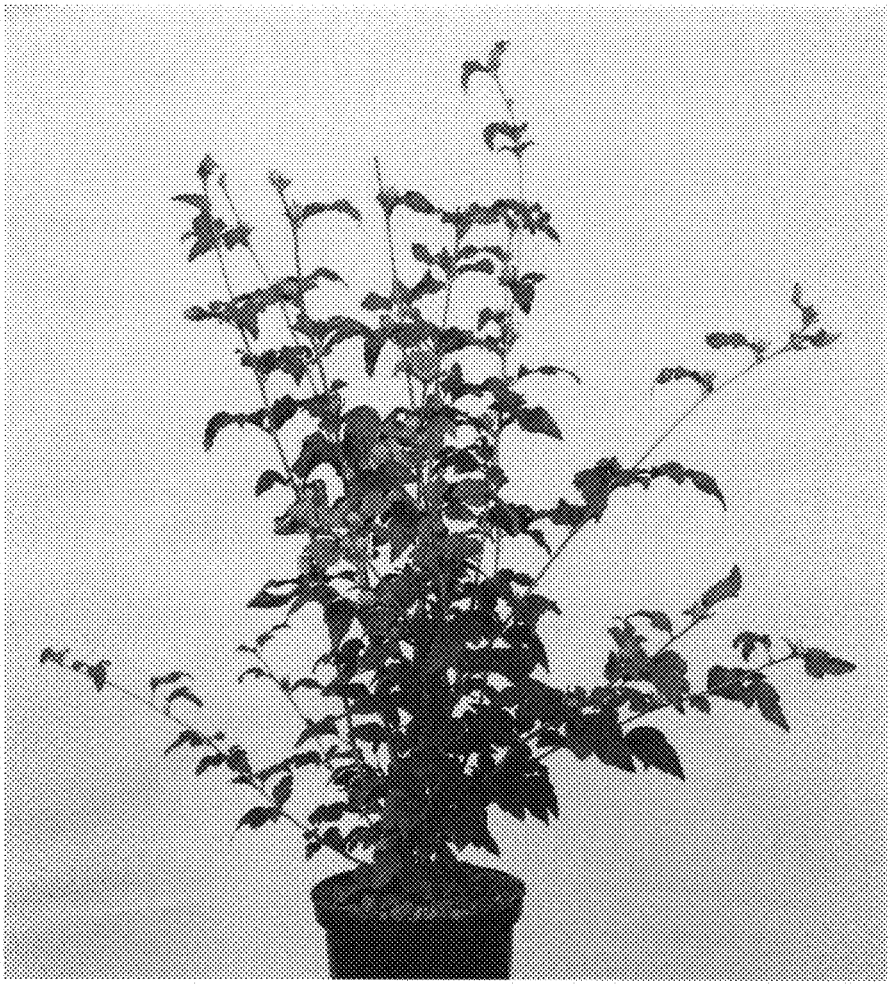

Latin name of the genus and species: *Hibiscus syriacus*. Variety denomination: 'RWOODS5'.

BACKGROUND OF THE INVENTION

The new *Hibiscus* cultivar is a product of a planned breeding program conducted by the inventor, Roderick Ian Woods. The objective of the breeding program was to produce new *Hibiscus syriacus* varieties with double or semi-double flowers on vigorous plants. The cross resulting in this new variety was made during 2006.

The seed parent is the unpatented proprietary *Hibiscus syriacus* '7060'. The pollen parent is the unpatented proprietary variety *Hibiscus syriacus* '5954'. The new variety was identified as a potentially interesting selection in September 2008, with the inventor continuing variety observations and finally selecting the variety in 2011. Selection was made at a research nursery in Norfolk, the United Kingdom.

Asexual reproduction of the new cultivar 'RWOODS5' was first performed in January 2009 in Norfolk, UK. Vegetative soft wood cuttings were grafted onto an unnamed, unpatented *Hibiscus syriacus* rootstock. Subsequent propagation has shown that the unique features of this cultivar are stable and reproduced true to type in 6 successive generations.

SUMMARY OF THE INVENTION

The cultivar 'RWOODS5' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RWOODS5' These characteristics in combination distinguish 'RWOODS5' as a new and distinct *Hibiscus* cultivar:

1. Bright magenta flower color, near RHS Red-Purple 71B.
2. Full, double flowers.
3. Distinctive manner of opening petals, outer petals open so fully to form a nearly flat flower base.
4. Large flowers up to 10 cm in diameter
5. Vigorous plants with good resistance to wet weather.
6. Floriferous plants.

PARENT COMPARISON

Plants of the new cultivar 'RWOODS5' are similar to plants of the seed parent variety in most horticultural characteristics, however, plants of the new cultivar 'RWOODS5' differ in the following;

1. The new variety has darker flowers than the seed parent, 71B compared to 68C.
2. The new variety has a fully double flower, the center of the flower is completely filled with petaloids. The seed parent has a semi-double flower, with a small amount of central petaloids.
3. The new variety produces flowers up to 10 cm in diameter, the seed parent flowers can reach 12 cm in diameter.

Plants of the new cultivar 'RWOODS5' are similar to plants of the pollen parent variety *Hibiscus syriacus,* '5954' in most horticultural characteristics, however, plants of the new cultivar 'RWOODS5' differ in the following;

1. The new variety has darker flower flowers than the pollen parent, 71B compared to 64D.
2. The new variety has a well formed, fully double flower, with both fully formed outer petals and proportionately sized petaloids, the pollen parent has a poorly formed flower with large central petaloids.
3. The new variety produces flowers up to 10 cm in diameter, the pollen parent flowers can reach 7 cm in diameter.

COMMERCIAL COMPARISON

Plants of the new cultivar 'RWOODS5' can be compared to the variety *Hibiscus* 'Lucy', unpatented. These varieties are similar in most horticultural characteristics however, 'RWOODS5' differs in the following:

1. Flower color of the new variety is near Red-Purple 71B, compared to Red 52 flowers of this comparator.

BRIEF DESCRIPTION OF THE PHOTOGRAPHS

The accompanying photograph in FIG. 1 illustrates in full color a typical plant of 'RWOODS5' grown in an approximately 8 inch pot, in the Netherlands.

Figure 2:
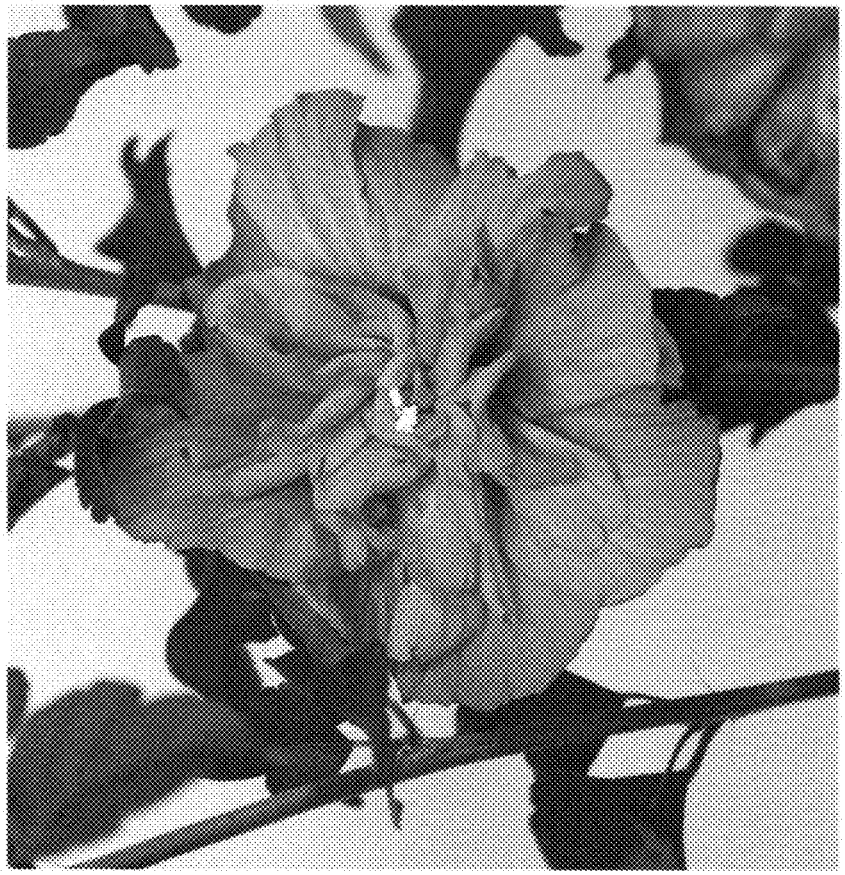

FIG. 2 illustrates in full color a typical flower of 'RWOODS5'. Age of the plant photographed is approximately 1.5 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'RWOODS5' plants grown in an unheated greenhouse in the Netherlands, under natural lighting. Measurements were taken during the August of 2015. The plants were 2 years old in 21 cm containers. The growing temperature ranged from approximately −5° C. to 27° C. Measurements and numerical values represent averages of typical plant types.

Botanical classification: *Hibiscus syriacus* 'RWOODS5'.

PROPAGATION

Time to initiate roots: 20 days at approximately 25° C.

Root description: Fibrous, medium root thickness. Tan/brown in color, not effectively measured with a color chart.

Time to produce a rooted young plant: About 90 days at 25° C.

PLANT

Plant type: Perennial shrub.

Age of plant described: Approximately 2 years old.

Growth habit: Upright

Pot size of plant described: 3 gallon pot.

Overall plant shape: Upright, broad ovate.

Height: 86.5 cm.

Plant spread: 81 cm.

Growth rate: Approximately 15 cm during Spring months of active growth.

Plant vigor: Moderate to high.

Branching characteristics: Branching near base. Some pinching required to encourage a denser plant habit.

Length of primary lateral branches: 60.9 cm.

Diameter of lateral branches: 4 mm.

Quantity of lateral branches: Average 14.

Stem:

- *Stem shape*.—Round.
- *Stem strength*.—Moderate.
- *Color*.—Stem: Near RHS Greyed-Green 194B. Bark: Near RHS Grey-brown 197B.
- *Pubescence*.—Glabrous.
- *Angle of attachment*.—Average angle 60° from center of plant.

Internode length: 5.3 cm on average.

FOLIAGE

Leaf:

- *Arrangement*.—Alternate, single.
- *Leaf shape*.—Overall ovate, tri-lobed.
- *Average length*.—8.4 cm.
- *Average width*.—6.1 cm.
- *Apex*.—Bluntly narrowly acute.
- *Base*.—Obtuse.
- *Margin*.—Lobed and coarsely crenate.
- *Variegation*.—Absent.
- *Texture of top surface*.—Smooth.
- *Texture of bottom surface*.—Smooth. Main veins and secondary veins with sparse adpressed hairs.
- *Color*.—Young foliage upper side: Between RHS Green 141B and 143A. Young foliage under side: Near RHS Green 143A. Mature foliage upper side: Near RHS Yellow-green 147A. Mature foliage under side: Green to yellow-Green, between 137C and 147B.
- *Venation*.—Pattern: Palmate. Color upper side: Near RHS Green 143B. Color under side: Near RHS Yellow-green 144C.
- *Petiole*.—Average Length: 1.4 cm. Diameter: 1.5 mm. Petiole color upper side: Near RHS Green 137C. Petiole color lower side: Near RHS Green 137C. Petiole Texture upper side: Smooth. Petiole Texture lower side: Smooth.

FLOWER

Natural flowering season: Early June through Summer continuously.

Flowering form: Fully double, rotate.

Flower habit: Solitary, emerging from leaf axils.

Flower longevity on plant: About 4 days.

Quantity of flowers per plant: About 50 flowers and buds on a mature plant in full bloom.

Flower shape: Overall shape is a half dome.

Rate of flower opening: Approximately 5 days from bud stage described to open flower.

Flower aspect: Upright and slightly outward.

Size:

- *Length*.—10 cm.
- *Diameter*.—5 cm.
- *Depth*.—5.9 cm.

Flower other characteristics:

- *Persistence*.—Self-cleaning.
- *Fragrance*.—None.
- *Eye zone*.—Absent.

Bud:

- *Shape*.—Rounded cone.
- *Length*.—Average 2.0 cm.
- *Diameter*.—Average 1.5 cm.
- *Color*.—Near Greyed-Green 191B, upper section Greyed-Purple 187A.

Petal:

- *Petal arrangement*.—Whorled and a thick central whorl of petaloids.

*Number of petals per flower.*—5 large outer petals.
*Fused.*—No.
*Petal shape.*—Broad obovate.
*Petal base.*—Truncate.
*Margin.*—Entire.
*Tip shape.*—Irregular, finely repand.
*Attitude.*—Horizontal.
*Length.*—5.8 cm.
*Width.*—5.4 cm.
*Texture.*—Upper: Glabrous. Lower: Glabrous.
*Appearance.*—Upper surface matte with glossy base. Lower surface matte.
*Undulation.*—Medium.

Petal color:
*When opening.*—Upper surface: Main surface a mixture of Red-purple 72D, N74C and N74D. Near apex mixture of Red-Purple 64C, 64D, 71C and 71D. Base Between Red 53A and Red-Purple 59A. Lower surface: Near RHS Purple 60C, base near Red 53B.
*Fully opened.*—Upper surface: Main surface a mixture of Red-Purple 72D, N74C and N74D. Near apex mixture of Red-Purple 64C, 64D, 71C and 71D. Base Between Red 53A and Red-Purple 59A. Lower surface: Near RHS Purple 60C, base near Red 53B.
*Fading to.*—Upper surface: Near RHS Purple N74C, base 59A. Lower surface: Near RHS Purple N74C, base 59A.

Petaloids:
*Arrangement.*—Thick central whorl of petaloids at the base of the style and along the style.
*Number of petaloids per flower.*—Average 50.
*Shape.*—Oblanceolate.
*Base.*—Truncate.
*Margin.*—Entire.
*Tip shape.*—Obtuse to broadly acute, irregularly lobed.
*Length.*—3.8 cm.
*Width.*—1.4 cm.
*Texture.*—Upper: Glabrous. Lower: Glabrous.
*Appearance.*—Upper surface matte with glossy base. Lower surface matte.

Petaloid color:
*When opening.*—Upper surface: Near Red-purple N74D. Base near Red 53A. Lower surface: Near Red-purple N74D. Base near Red 53A.
*Fully opened.*—Upper surface: Near Red-purple N74D. Base near Red 53A. Lower surface: Near Red-purple N74D. Base near Red 53A.

Sepal:
*Arrangement.*—Rotate, lower 50% fused.
*Number.*—Average 5.
*Shape.*—Elliptic to ovate.
*Tip.*—Acute.
*Base.*—Fused.
*Margin.*—Entire.
*Length.*—2.0 cm.
*Width.*—1 cm.
*Texture, upper.*—Rough; slightly pubescent.
*Texture, lower.*—Smooth; waxy.
*Color.*—Immature: Upper surface: Yellow-Green 144C. Under surface: Near Greyed-Green 191B. Mature: Upper surface: Near Green 143C, base near yellow-Green 144C. Under surface Calyx: Near RHS Green 137D.

Calyx:
*Shape.*—Rotate.
*Length.*—1.7 cm.
*Diameter.*—2 cm.

Peduncle:
*Length.*—2.7 cm.
*Diameter.*—2.5 mm.
*Color.*—Near RHS Green 137C.
*Orientation.*—40°.
*Strength.*—Moderate.
*Texture.*—Glabrous.

Bracts: Occurring at the base of each flower is a ring of bracts, pressed against the sepals.
*Quantity.*—Average 7 per ring.
*Shape.*—Linear.
*Length.*—Average 2.4 cm.
*Width.*—Average 1.5 mm.
*Color.*—Upper surface near Green N137A, lower surface near 143A.

REPRODUCTIVE ORGANS

Stamens:
*Number.*—Average 15, clustered and implanted in style, typical of *Hibiscus*.
*Filament length.*—2.5 mm.
*Filament color.*—Near RHS White N155D.

Anthers:
*Shape.*—Dorsifixed.
*Length.*—2 mm.
*Color.*—Near RHS Orange-White 159A.
*Pollen color.*—Near RHS Yellow 11B.
*Pollen amount.*—Abundant.

Pistil:
*Number.*—1.
*Length.*—3.9 cm.
*Style.*—Length: 3.7 cm. Color: Near RHS White N155D.
*Stigma.*—Shape: Club-shaped, typically 5 stigmas. Color: Near RHS White 155B.
*Ovary color.*—Near RHS Yellow-Green 150C.

OTHER CHARACTERISTICS

Seeds and fruits: Not observed to date.

Disease/pest resistance: Neither resistance nor susceptibility to normal diseases and pests of *Hibiscus syriacus* have been observed.

Garden performance: Good tolerance, performs well in humid conditions.

Temperature tolerance: Low temperature tolerance to at least USDA zone 4, high temperature tolerance to at least 40° C.

What is claimed is:

1. A new and distinct cultivar of *Hibiscus* plant named 'RWOODS5' as herein illustrated and described.

* * * * *